United States Patent [19]

Fessler et al.

[11] 4,099,010

[45] Jul. 4, 1978

[54] PHTHALOYL AMINO ACID HYDROXAMIC ACIDS

[75] Inventors: Dyral C. Fessler, Norwich, N.Y.; Edwin R. Micalizzi, Allegan, Mich.

[73] Assignee: Morton-Norwich Products, Inc., Norwich, N.Y.

[21] Appl. No.: 777,953

[22] Filed: Mar. 16, 1977

Related U.S. Application Data

[60] Division of Ser. No. 711,626, Aug. 4, 1976, which is a continuation-in-part of Ser. No. 625,915, Oct. 28, 1975, abandoned.

[51] Int. Cl.² .................... C07D 233/64;
[52] U.S. Cl. ................ 548/344; 260/518 R; 424/273 R; 424/319

[58] Field of Search .................... 548/344;

[56] References Cited

U.S. PATENT DOCUMENTS 3,468,936   9/1969   van der Burg .................... 548/344

OTHER PUBLICATIONS

Helferich et al. Chem. Ber. 1959, vol. 92, pp. 2813–2827.

*Primary Examiner*—Natalie Trousof
*Attorney, Agent, or Firm*—Anthony J. Franze

[57] ABSTRACT

A series of phthaloyl amino acid hydroxamic acids are useful as inhibitors of Angiotensin I converting enzyme.

1 Claim, No Drawings

PHTHALOYL AMINO ACID HYDROXAMIC ACIDS

This application is a division of our copending application Ser. No. 711,626, filed Aug. 4, 1976, which is a continuation-in-part of our application Ser. No. 625,915, filed Oct. 28, 1975, now abandoned.

This invention is concerned with chemical compounds and particularly with phthaloyl amino acid hydroxamic acids of the formula:

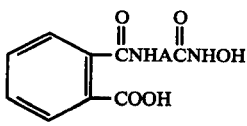

wherein A is methylene, ethylene or

wherein R is methyl, imidazolylmethyl, isobutyl, benzyl or 4-aminobutyl and in which

is in the D-configuration.

The members of this series are potent inhibitors of the enzyme responsible for the conversion of Angiotensin I to the powerful pressor agent Angiotensin II associated with hypertension. They are thus capable of interrupting the biological pathway leading to the formation of that active pressor substance. For example, they inhibit the pure converting enzyme isolated from rabbit lung tissue at levels of from 0.8 to $1.9 \times 10^{-5}$ moles per liter.

The compounds of this invention are also capable of inhibiting the hypertensive effects induced by administration of Angiotensin I to animals. Infusion of these compounds at a rate of from 0.5 to 10 μg./kg./min. intravenously in physiologically acceptable menstrua such as isotonic saline to pithed rats counteracts the elevation in blood pressure induced by Angiotensin I by at least 50%.

The method which is currently preferred for the preparation of the compounds of this invention is shown by the following equation:

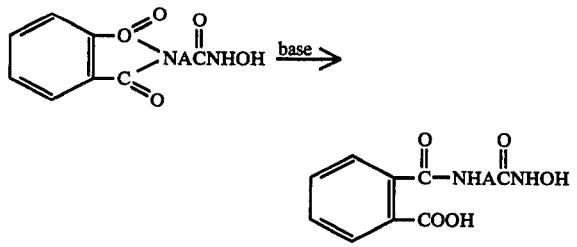

wherein A has the significance given above. The base employed is an inorganic one such as potassium hydroxide.

In order that this invention may be readily available to and understood by those skilled in the art, the following examples of the preparation of the compounds thereof are appended.

EXAMPLE I 3-(2-Carboxybenzamido)Propionohydroxamic Acid

A. Phthaloyl-β-Alanine Hydroxamic Acid

Phthaloyl-β-alanine (15.3 g, 0.07 m) was dissolved in dichloromethane (100 ml) and dimethylformamide (10 ml), cooled and a solution of dicyclohexylcarbodiimide (14.4 g, 0.07 m) in dichloromethane (50 ml) was added. In another flask hydroxylamine hydrochloride (4.87 g, 0.077 m) was dissolved in dimethylformamide (70 ml), and triethylamine (10.75 ml, 0.077 m) was added. The mixture was cooled and filtered. The filtrate was added to the above cold stirred solution, refrigerated overnight, filtered and the filtrate evaporated to dryness. The residue was crystallized from methanol/ethyl acetate. Yield: 13.0 g.

Recrystallization from ethyl acetate/petroleum ether gave the product, m.p. 146°.

Anal. Calcd. for $C_{11}H_{10}N_2O_4$: C, 56.41; H, 4.30; N, 11.96; Found: C, 56.15; H, 4.50; N, 11.79.

B. 3-(2-Carboxybenzamido)propionohydroxamic Acid

Potassium hydroxide (1.44 g, 26 mMol) was dissolved in water (50 ml), phthaloyl-β-alanine hydroxamic acid (2.0 g. 8.6 mMol) added; stirred at room temperature 3 hours and chromatographed on a 12 g acid ion exchange column. Fractions containing product were combined and lyophilized, yielding 1.8 g, m.p. 58°–65°.

Anal. Calcd. for $C_{11}H_{12}N_2O_5$: C, 52.38; H, 4.80; N, 11.11; Found: C, 52.34; H, 5.13; N, 10.65.

EXAMPLE II

N-(2-Carboxybenzoyl)-D-Alanine Hydroxamic Acid

Phthaloyl-D-alanine (15.0 g, 0.069 m) was dissolved in dichloromethane (100 ml) and dimethylformamide (10 ml), cooled, a solution of dicyclohexylcarbodiimide (14.19 g, 0.069 m) in dichloromethane (50 ml) added. In another flask hydroxylamine hydrochloride (5.28 g, 0.076 m) was dissolved in dimethylformamide (70 ml), triethylamine (10.6 ml, 0.076 m) added, cooled, and filtered. The filtrate was added to the above cold stirred solution, refrigerated overnight, filtered and evaporated to an oil. The oil was chromatographed on a 150 g silica gel column with 5% methanol/chloroform. The fractions containing product were combined and evaporated to an oil, which crystallized from ethyl acetate yielding 4.3 g, m.p. 157° (dec.), of phthaloyl-D-alanine hydroxamic acid.

Anal. Calcd. for $C_{11}H_{10}N_2O_4$: C, 56.41; H, 4.30; N, 11.96; Found: C, 56.14; H, 4.28; N, 11.81.

Potassium hydroxide (3.39 g. 60.3 mMol) was dissolved in water (50 ml) and phthaloyl-D-alanine hydroxamic acid (4.7 g, 20.1 mMol) added. The resulting solution was stirred at room temperature 2 hours, chromatographed on a 25 g acid ion exchange column, and fractions containing product lyophilized to yield: 4.9 g $[\alpha]_D^{21°} = +29.2°$ (C=1.02, $H_2O$).

Anal. Calcd. for $C_{11}H_{12}N_2O_5$: C, 52.38; H, 4.80; N, 11.11; Found: C, 51.85; H, 4.83; N, 10.75.

EXAMPLE III

N-(2-Carboxybenzoyl)-D-histidine Hydroxamic Acid

Potassium hydroxide (11.5 g, 0.205 m) was dissolved in methanol (75 ml) and added to a solution of hydroxylamine hydrochloride (7.16 g, 0.103 m) in methanol (50 ml). The resulting mixture was filtered, the filtrate added to a solution of methyl-D-histidinate dihydrochloride (10.0 g, 0.41 m) in methanol (100 ml), and stirred at room temperature 18 hours. The solution was then filtered, evaporated and the residue crystallized from water yielding 5.0 g, m.p. 150°-151° (dec.) of D-histidine hydroxamic acid.

D-Histidine hydroxamic acid (1.9 g, 11.2 mMol) was dissolved in dimethylformamide (75 ml) and water (100 ml). Phthalic anhydride (1.65 g, 11.2 mMol) was added, the solution stirred 4 hours, evaporated to an oil which was crystallized from water/ethanol, and crystallized again from water to yield 1.6 g, m.p. 175° (dec.) of N-(2-carboxybenzoyl)-D-histidine hydroxamic acid.

Anal. Calcd. for $C_{14}H_{14}N_4O_5$: C, 52.83; H, 4.43; N, 17.61; Found: C, 52.42; H, 4.51; N, 17.46.

EXAMPLE IV

N-(2-Carboxybenzoyl)-D-leucine Hydroxamic Acid

A. Phthaloyl-D-leucine Hydroxamic Acid

Phthaloyl-D-leucine (15.0 g, 0.058 m) was dissolved in dichloromethane (100 ml) and dimethylformamide (10 ml), cooled and a solution of dicyclohexylcarbodiimide (11.95 g, 0.058 m) in dichloromethane (50 ml) was added. In another flask hydroxylamine hydrochloride (4.45 g, 0.064 m) was dissolved in dimethylformamide (70 ml), triethylamine (9.0 ml, 0.064 m) was added and the mixture was cooled and filtered. The filtrate was added to the above cold stirred solution which was then refrigerated overnight, filtered and evaporated to an oil. This oil was chromatographed on a 150 g silica gel column with 5% methanol/chloroform. Fractions containing product were combined and evaporated to an oil, which crystallized from chloroform/petroleum ether, yielding 5.2 g, m.p. 134°-136° of phthaloyl-D-leucine hydroxamic acid.

Anal. Calcd. for $C_{14}H_{16}N_2O_4$: C, 60.86; H, 5.84; N, 10.14; Found: C, 60.49; H, 5.82; N, 10.12.

Potassium hydroxide (2.45 g, 43.5 mMol) was dissolved in water (50 ml) and phthaloyl-D-leucine hydroxamic acid (4.0 g, 14.5 mMol) added. After stirring 2 hours at room temperature, the solution was chromatographed on a 25 g acid ion exchange column. The fractions containing product crystallized to yield: 2.7 g, m.p. 156° (dec.), $[\alpha]_D^{22°} = +64.5°$ (C=1.10, MeOH).

Anal. Calcd. for $C_{14}H_{18}N_2O_5$: C, 57.13; H, 6.16; N, 9.52; Found: C, 57.18; H, 6.23; N, 9.41.

EXAMPLE V

N-(2-Carboxybenzoyl)-D-phenylalanine Hydroxamic Acid Hemihydrate

Phthaloyl-D-phenylalanine (15.0 g, 0.051 m) was dissolved in dichloromethane (100 ml) and dimethylformamide (10 ml), cooled and a solution of dicyclohexylcarbodiimide (10.51 g, 0.04 m) in dichloromethane (50 ml) was added. In anther flask hydroxylamine hydrochloride (3.89 g, 0.056 m) was dissolved in dimethylformamide (70 ml), triethylamine (7.85 ml), 0.056 m) was added and the mixture cooled and filtered. The filtrate was added to the above cold stirred solution, which was then refrigerated overnight, filtered and evaporated to an oil. The oil was dissolved in dichloromethane (100 ml), treated with charcoal, filtered, washed with cold water (2 × 50 ml), dried over magnesium sulfate, and evaporated to an oil. This oil was chromatographed on a 150 g silica gel column, with 5% methanol/chloroform. The fractions containing product were combined and evaporated to an oil, which crystallized from ethyl acetate/petroleum ether, yielding 3.5 g, m.p. 159° (dec.) of phthaloyl-D-phenylalanine hydroxamic acid.

Anal. Calcd. for $C_{17}H_{14}N_2O_4$: C, 65.80; H, 4.55; N, 9.03; Found: C, 65.36; H, 4.42; N, 8.62.

Potassium hydroxide (2.99 g, 53.1 mMol) was dissolved in water (50 ml) and phthaloyl-D-phenylalanine hydroxamic acid (5.5 g, 17.7 mMol) was added. The solution was stirred at room temperature 2 hours, and then acidified to pH 2–3 with 6N sulfuric acid. Ethyl acetate (25 ml) was added and the product filtered. The water layer was separated and extracted twice more with ethyl acetate (25 ml). The ethyl acetate layers were combined, dried over magnesium sulfate and evaporated to an oil. The solid product and oil were crystallized separately from ethyl acetate/petroleum ether, filtered and recrystallized separately again from ethyl acetate/petroleum ether, to yield respectively 1 g and .7 g, m.p. 135° (dec.), $[\alpha]_D^{22°} = +61.65°$ (C=1.09, MeOH) of N-(2-carboxybenzoyl)-D-phenylalanine hydroxamic acid hemihydrate.

Anal. Calcd. for $C_{17}H_{16}N_2O_5 \cdot \frac{1}{2} H_2O$: C, 60.53; H, 5.09; N, 8.31; $H_2O$, 2.7%; Found: C, 60.78; H, 5.18; N, 8.22; $H_2O$, 3.1%.

EXAMPLE VI

N-(2-Carboxylbenzoyl)-D-Lysine Hydroxamic Acid Dihydrate

Phthaloyl-$N^\epsilon$-trifluoroacetyl-D-lysine (17.9 g, .048 ml) was dissolved in dichloromethane (100 ml) and dimethylformamide (20 ml), cooled and dicyclohexylcarbodiimide (9.9 g, .048 ml) in dichloromethane (25 ml) was added. Hydroxylamine hydrochloride (3.68 g, 0.053 m) was dissolved in dimethylformamide (50 ml), triethylamine (7.4 ml, .053 m) added, the mixture cooled and filtered. The filtrate was added to the above cold, stirred solution and refrigerated overnight, filtered and evaporated to an oil. This oil was chromatographed on a 175 g methanol deactivated silica gel column, with 5% methanol/chloroform. Fractions containing product were combined, evaporated and crystallized from ethyl acetate/petroleum ether to yield 6.7 g, m.p. 144° (dec.) of phthaloyl-N-trifluoroacetyl-D-lysine hydroxamic acid.

Anal. Calcd. for $C_{16}H_{16}N_3O_5F_3$: C, 49.62; H, 4.16; N, 10.85; Found: C, 49.34; H, 4.21; N, 10.43.

Potassium hydroxide (2.44 g, .0435 m) was dissolved in water (50 ml) phthaloyl-$N^\epsilon$-trifluoroacetyl-D-lysine hydroxamic acid (5.6 g, 0.0145 m) was added, stirred 2 hours at room temperature, and chromatographed on a 50 g acid ion exchange resin column. Fractions containing product were combined, filtered, lyophilized and crystallized from methanol to yield 2.45 g, m.p. 159° (dec.), of N-(2-carboxybenzoyl-D-lysine hydroxamic acid dihydrate.

Anal. Calcd. for $C_{14}H_{19}N_3O_5 \cdot 2 H_2O$: C, 48.69; H, 6.71; N, 12.17; $H_2O$, 10.4%; Found: C, 49.01, H, 6.52; N, 12.14; $H_2O$, 10.22%.

EXAMPLE VII (2-Carboxybenzamido)acetohydroxamic acid

Phthaloylglycine (43.1 g, 0.21 m) was dissolved in dichloromethane (300 ml) and dimethyl formamide (30 ml). The mixture was cooled and dicyclohexylcarbodiimide (44.2 g, 0.21 m) dissolved in dichloromethane (100 ml) was added. In a separate flask a mixture of hydroxylamine hydrochloride (16.05 g, 0.23 m), triethylamine (32.3 g, 0.23 m) and dimethylformamide (200 ml) was prepared, cooled, filtered and the filtrate added to the above cold, stirred solution. After standing in a refrigerator overnight, the mixture was filtered and the filtrate was evaporated to an oil which crystallized from methanol/ethyl acetate to yield 17 g, m.p. 167° (dec.), of 2-phthalamidoacetohydroxamic acid.

Anal. Calcd. for $C_{18}H_8N_2O_4$: C, 54.55; H, 3.66; N, 12.72; Found: C, 54.37; H, 3.70; N, 12.77.

A mixture of 2-phthalamidoacetohydroxamic acid (1.1 g, 5 mMol), KOH (0.84 g, 15 mMol) in water (10 ml) was stirred at room temperature for 2 hours, filtered and acidified with N $H_2SO_4$. The product (0.6 g) crystallized upon cooling. Recrystallization from water gave (2-carboxybenzamido) acetohydroxamic acid, m.p. 157° (dec.).

Anal. Calcd. for $C_{10}H_{10}N_2O_5$: C, 50.42; H, 4.23; N, 11.76; Found: C, 50.38; H, 4.31; N, 11.67.

What is claimed is:

1. The compound N-(2-carboxybenzoyl)-D-histidine hydroxamic acid.

* * * * *